(12) United States Patent
Chung et al.

(10) Patent No.: US 7,718,174 B2
(45) Date of Patent: May 18, 2010

(54) ANTI-HGF/SF HUMANIZED ANTIBODY

(75) Inventors: Junho Chung, Gyeongsangbuk-do (KR); Kisu Kim, Seoul (KR)

(73) Assignee: Abxign, Inc., Seoul (KR)

( * ) Notice: Subject to any disclaimer, the term of this patent is extended or adjusted under 35 U.S.C. 154(b) by 293 days.

(21) Appl. No.: 11/626,055

(22) Filed: Jan. 23, 2007

(65) Prior Publication Data

US 2008/0038256 A1    Feb. 14, 2008

(30) Foreign Application Priority Data

Jul. 14, 2006    (KR) .................. 10-2006-0066241

(51) Int. Cl.
*A61K 39/395* (2006.01)
*C12P 21/08* (2006.01)
(52) U.S. Cl. .................. 424/133.1; 530/387.3
(58) Field of Classification Search ........... None
See application file for complete search history.

(56) References Cited

U.S. PATENT DOCUMENTS 7,408,043 B2 * 8/2008 Chung et al. ............. 530/388.1

FOREIGN PATENT DOCUMENTS

WO          2005/044848         5/2005
WO     WO 2005/044848 A1 *    5/2005

OTHER PUBLICATIONS

Manuela Zaccolo et al., Dimerization of Fab fragments enables ready screening of phage antibiotics that effect hepatocyte growth factor/scatter factor activity on target cells, Eur. J. Immunol., 27: 618-623(1997), In English.

George A. Stouffer et al., Inflammation, Growth Regulatory Molecules & Atherosclerosis, Journal of Cellular Biochemistry, Supplement 18A: 288(1994), In English.

Brian Cao et al., Neutralizing monoclonal antibodies to hepatocyte growth factor/scatter factor (HGF/SF) display antitumor activity in animal models, Proceedings of the National Academy of Sciences, 98(13): 7443-7448 (2001), In English.

Massimo Di Nicola et al., Human bone marrow stromal cells suppress T-lymphocyte proliferation induced by cellular or nonspecific mitogenic stimuli, Blood, 99(10): 3838-3843 (2002), In English.

Andrew W. Burr et al., Anti-Hepatocyte Growth Factor Antibody Inhibits Hepatocyte Proleferation During Liver Regeneration, Journal of Pathology, 185:298-302 (1998), In English.

Keiji Miyazawa, Functions and Diseases of Cell Proliferation factor, Yodosha: 58-64 (1998), partial translation.

Nobuhiko Kasai, Introduction to Immunology, Kodansha: 41-42 (1989), Partial translation.

* cited by examiner

*Primary Examiner*—Marianne P Allen
(74) *Attorney, Agent, or Firm*—Sughrue Mion, PLLC

(57) ABSTRACT

The inventive anti-HGF/SF humanized antibody prepared by displaying on the surface of a phage an anti-HGF/SF chimeric Fab library comprising a set of human antibody light chain variable region ($V_L$) and human antibody heavy chain variable region ($V_H$) which are grafted with heavy chain complementary determining regions (HCDRs) of an anti-HGF/SF antibody of an animal other than human, has the equal or greater binding affinity than that of the parent anti-HGF/SF antibody, the neutralizing activity inhibiting the binding of HGF/SF to its receptor, cMET while having the reduced immunogenicity in human. Therefore, the inventive anti-HGF/SF humanized antibody can be used for preventing and treating diseases effectively, e.g., cancers, by the action of binding HGF/SF to cMET.

3 Claims, 5 Drawing Sheets

Fig. 2

```
VL domain
          FR 1                          CDR1            FR2                CDR2      FR3                                    CDR3              FR4
                  1         2         3         4         5         6         7         8         9         1
          1234567890123 4567890123 4 56789012345678 0123456 789012345678901234567890123456789012345678 90123456 7890123456789
SFN 68    ELDLTQTPSSVSAAVGGTVTINC QASQSVSNLLA WYQQKPGQPPKLLIY GASWLES GVPSRFRGSGSGTEFTLTISGHKAEDAATYYC QSGYYSAGA TFGAGTWVEIKR
13        ---QH-S---L-S--DR--T-- R----I-TW-- -------KA------ K-T---- ---L-S-G---D------SLQS--F---F- -QSYSLPP- ---Q--K--V--
16        ---VH-S---TL-S--DR--T-- R----I-SW-- -------KA------ K-T---- ---S-S-G---E------SLQPD-F----- -QYSRYSGG ---Q--K--R--
27        ---QH-S---TL-S--DR--T-- R----I-SR-- -------KA------ R-T--G- ---S-S---E--------LQPD-F----- -QYSTFSP- ---Q--Q--D--
41        ---QH-S------S--DR--S-- R---DIRS--- -------KA------ K-T---- ---S-S---E--------HLQPD-F----- -QYSRYSGG ---Q--K--R--
```

SEQUENCE LISTING

```
<160> NUMBER OF SEQ ID NOS: 40

<210> SEQ ID NO 1
<211> LENGTH: 5
<212> TYPE: PRT
<213> ORGANISM: Artificial Sequence
<220> FEATURE:
<223> OTHER INFORMATION: amino acid sequence of HCDR1 of anti-HGF/SF
      humanized antibody

<400> SEQUENCE: 1

Thr Tyr Tyr Met Ser
1               5

<210> SEQ ID NO 2
<211> LENGTH: 17
<212> TYPE: PRT
<213> ORGANISM: Artificial Sequence
<220> FEATURE:
```

-continued

```
<223> OTHER INFORMATION: amino acid sequence of HCDR2 of anti-HGF/SF
      humanized antibody

<400> SEQUENCE: 2

Tyr Ile Gly Thr Ser Ser Gly Thr Thr Tyr Tyr Ala Asn Ser Val Lys
 1               5                  10                  15

Gly

<210> SEQ ID NO 3
<211> LENGTH: 7
<212> TYPE: PRT
<213> ORGANISM: Artificial Sequence
<220> FEATURE:
<223> OTHER INFORMATION: amino acid sequence of HCDR3 of anti-HGF/SF
      humanized antibody

<400> SEQUENCE: 3

Gly Leu Gly Arg Ile Asn Leu
 1               5

<210> SEQ ID NO 4
<211> LENGTH: 108
<212> TYPE: PRT
<213> ORGANISM: Artificial Sequence
<220> FEATURE:
<223> OTHER INFORMATION: amino acid sequence of VL of clone HSFN 68-13

<400> SEQUENCE: 4

Glu Leu Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Thr Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Glu Ser Gly Val Pro Leu Arg Phe Ser Gly
    50                  55                  60

Gly Gly Ser Gly Thr Asp Phe Thr Leu Thr Ile Ser Ser Leu Gln Ser
65                  70                  75                  80

Glu Asp Phe Ala Thr Tyr Phe Cys Gln Gln Ser Tyr Ser Leu Pro Pro
                85                  90                  95

Thr Phe Gly Gln Gly Thr Lys Val Glu Val Lys Arg
            100                 105

<210> SEQ ID NO 5
<211> LENGTH: 116
<212> TYPE: PRT
<213> ORGANISM: Artificial Sequence
<220> FEATURE:
<223> OTHER INFORMATION: amino acid sequence of VH of clone HSFN 68-13

<400> SEQUENCE: 5

Gln Gln Gln Leu Val Glu Ser Gly Gly Val Val Arg Pro Gly Gly
 1               5                  10                  15

Ser Leu Arg Leu Ser Cys Ala Ala Ser Gly Phe Thr Phe Ser Thr Tyr
            20                  25                  30

Tyr Met Ser Trp Val Arg Gln Ala Pro Gly Lys Gly Leu Glu Trp Ile
        35                  40                  45

Gly Tyr Ile Gly Thr Ser Ser Gly Thr Thr Tyr Tyr Ala Asn Ser Val
    50                  55                  60

Lys Gly Arg Phe Thr Ile Ser Ser Asp Asn Ala Lys Asn Ser Val Tyr
65                  70                  75                  80
```

Leu Gln Met Asn Ser Leu Arg Pro Glu Asp Thr Ala Val Tyr Tyr Cys
                85                  90                  95

Ala Arg Gly Leu Gly Arg Ile Asn Leu Trp Gly Pro Gly Thr Leu Val
            100                 105                 110

Thr Val Ser Ser
        115

<210> SEQ ID NO 6
<211> LENGTH: 324
<212> TYPE: DNA
<213> ORGANISM: Artificial Sequence
<220> FEATURE:
<223> OTHER INFORMATION: nucleotide sequence of VL of clone HSFN 68-13

<400> SEQUENCE: 6
gagctccaga tgacccagtc tccatcctcc ctgtctgcat ctgtaggaga cagagtcacc    60
atcacttgcc gggccagtca gagtattagt acctggttgg cctggtatca gcagaaacca   120
gggaaagccc ctaagctcct gatctataag gcgtctactt tagaaagtgg ggtcccatta   180
agattcagcg gcgtggatc tgggacagat ttcactctca ccatcagcag cctgcaatcc   240
gaagattttg caacatattt ctgtcaacag agttacagtc ccctccgac attcggccag   300 gggaccaagg tcgaggtcaa acga                                          324

<210> SEQ ID NO 7
<211> LENGTH: 348
<212> TYPE: DNA
<213> ORGANISM: Artificial Sequence
<220> FEATURE:
<223> OTHER INFORMATION: nucleotide sequence of VH of clone HSFN 68-13

<400> SEQUENCE: 7
cagcagcagc tggtggagtc tgggggaggt gtagttcggc ctgggggtc cctgagactc    60 tcctgtgcag cctctggatt caccttcagt acctactaca tgagctgggt ccgccaggct   120
ccagggaagg gctagagtg gatcggatac attggtacta gtagtggtac cacttactac   180
gcgaactctg tgaagggccg attcaccatc tccagcgaca cgccaagaa ttccgtatat   240 ctgcaaatga acagtctgag acctgaggac acggccgtct attactgtgc aaggggggctg   300 ggcagaatta acttgtgggg ccaaggcacc ctggtcaccg tctcctca               348

<210> SEQ ID NO 8
<211> LENGTH: 109
<212> TYPE: PRT
<213> ORGANISM: Artificial Sequence
<220> FEATURE:
<223> OTHER INFORMATION: amino acid sequence of VL of clone HSFN 68-16

<400> SEQUENCE: 8

Glu Leu Val Met Thr Gln Ser Pro Ser Thr Leu Ser Ala Ser Val Gly
 1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Glu Ser Gly Val Ser Arg Phe Ser Gly
    50                  55                  60

Gly Gly Ser Gly Thr Glu Phe Thr Leu Thr Ile Ser Ser Leu Gln Pro
65                  70                  75                  80

```
Asp Asp Phe Ala Thr Tyr Tyr Cys Gln Gln Tyr Ser Arg Tyr Ser Gly
            85                  90                  95

Gly Thr Phe Gly Gln Gly Thr Lys Val Glu Ile Arg Arg
        100                 105

<210> SEQ ID NO 9
<211> LENGTH: 116
<212> TYPE: PRT
<213> ORGANISM: Artificial Sequence
<220> FEATURE:
<223> OTHER INFORMATION: amino acid sequence of VH of clone HSFN 68-16

<400> SEQUENCE: 9

Gln Gln Gln Leu Val Glu Ser Gly Gly Leu Val Gln Pro Gly Gly
 1               5                  10                  15

Ser Leu Arg Leu Ser Cys Ala Ala Ser Gly Phe Thr Phe Ser Thr Tyr
            20                  25                  30

Tyr Met Ser Trp Ile Arg Gln Ala Pro Gly Lys Gly Leu Glu Trp Ile
        35                  40                  45

Gly Tyr Ile Gly Thr Ser Ser Gly Thr Thr Tyr Tyr Ala Asn Ser Val
    50                  55                  60

Lys Gly Arg Phe Thr Ile Ser Ser Asp Asn Ala Gln Asn Ser Val Tyr
65                  70                  75                  80

Leu Gln Met Asn Ser Leu Arg Pro Glu Asp Thr Ala Val Tyr Tyr Cys
            85                  90                  95

Ala Arg Gly Leu Gly Arg Ile Asn Leu Trp Gly Gln Gly Thr Leu Val
            100                 105                 110

Thr Val Ser Ser
        115

<210> SEQ ID NO 10
<211> LENGTH: 327
<212> TYPE: DNA
<213> ORGANISM: Artificial Sequence
<220> FEATURE:
<223> OTHER INFORMATION: nucleotide sequence of VL of clone HSFN 68-16

<400> SEQUENCE: 10
gagctcgtga tgacccagtc tccttccacc ctgtctgcct ctgtaggaga cagagtcacc      60
atcacttgcc gggccagtca gagtattagt agctggttgg cctggtatca gcagaaacca     120
gggaaagccc ctaagctcct gatctataag gcgtctactt tagaaagtgg ggtctcatca     180
aggttcagcg gcggtggatc tgggacagaa ttcactctca ccatcagcag cctgcagcct     240
gatgattttg caacttatta ctgccaacag tatagtcgtt attcaggtgg gacgttcggc     300
caagggacca aggtggaaat cagacga                                         327

<210> SEQ ID NO 11
<211> LENGTH: 348
<212> TYPE: DNA
<213> ORGANISM: Artificial Sequence
<220> FEATURE:
<223> OTHER INFORMATION: nucleotide sequence of VH of clone HSFN 68-16

<400> SEQUENCE: 11
cagcagcagc tggtggagtc tgggggaggc ttggtacagc ctgggggggtc cctgagactc      60 tcctgtgcag cctctggatt caccttcagt acctactaca tgagctggat ccgccaggct     120
ccagggaagg ggctagagtg gatcggatac attggtacta gtagtggtac cacttactac     180
gcgaactctg tgaagggccg attcaccatc tccagcgaca acgcccagaa ttccgtatat     240
```

```
ttgcaaatga acagtctgag acctgaggac acggccgtct attactgtgc aagagggctg      300
ggcagaatta acttgtgggg ccaaggcacc ctggtcaccg tctcctca                   348
```

```
<210> SEQ ID NO 12
<211> LENGTH: 108
<212> TYPE: PRT
<213> ORGANISM: Artificial Sequence
<220> FEATURE:
<223> OTHER INFORMATION: amino acid sequence of VL of clone HSFN 68-27

<400> SEQUENCE: 12
```

Glu Leu Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Arg
            20                  25                  30

Leu Ala Trp Tyr Gln Gln Lys Pro Gly Lys Ala Pro Lys Leu Leu Ile
        35                  40                  45

Tyr Arg Ala Ser Thr Leu Glu Gly Gly Val Pro Ser Arg Phe Ser Gly
    50                  55                  60

Ser Gly Ser Gly Thr Glu Phe Thr Leu Thr Ile Ser Gly Leu Gln Pro
65                  70                  75                  80

Asp Asp Phe Ala Thr Tyr Tyr Cys Gln Gln Tyr Ser Thr Phe Ser Pro
                85                  90                  95

Thr Phe Gly Gln Gly Thr Gln Val Asp Ile Lys Arg
            100                 105

```
<210> SEQ ID NO 13
<211> LENGTH: 116
<212> TYPE: PRT
<213> ORGANISM: Artificial Sequence
<220> FEATURE:
<223> OTHER INFORMATION: amino acid sequence of VH of clone HSFN 68-27

<400> SEQUENCE: 13
```

Gln Val Gln Leu Val Glu Ser Gly Gly Gly Leu Val Lys Pro Gly Gly
 1               5                  10                  15

Ser Arg Arg Leu Ser Cys Ala Ala Ser Gly Phe Thr Phe Ser Thr Tyr
            20                  25                  30

Tyr Met Ser Trp Val Arg Gln Ala Pro Gly Lys Gly Leu Glu Trp Ile
        35                  40                  45

Gly Tyr Ile Gly Thr Ser Ser Gly Thr Thr Tyr Ala Asn Ser Val
    50                  55                  60

Lys Gly Arg Phe Thr Ile Ser Ser Asp Asn Ala Gln Asn Ser Val Tyr
65                  70                  75                  80

Leu Gln Met Asn Ser Leu Arg Pro Glu Asp Thr Ala Val Tyr Tyr Cys
                85                  90                  95

Ala Arg Gly Leu Gly Arg Ile Asn Leu Trp Gly Gln Gly Thr Leu Val
            100                 105                 110

Thr Val Ser Ser
        115

```
<210> SEQ ID NO 14
<211> LENGTH: 324
<212> TYPE: DNA
<213> ORGANISM: Artificial Sequence
<220> FEATURE:
<223> OTHER INFORMATION: nucleotide sequence of VL of clone HSFN 68-27

<400> SEQUENCE: 14
```

```
gagctccaga tgacccagtc tccttccacc ctgtctgcat ctgtgggaga cagggtcacc      60
atcacttgcc gggccagtca gagtattagt tcccggttgg cctggtatca gcagaaacca    120
gggaaagccc ctaaactgct aatctatcgg gcgtctactt tagaaggtgg ggtcccatca    180
agattcagcg gcagtggatc tgggacagaa ttcactctca ccatcagcgg cctgcagcct    240
gatgattttg caacttatta ctgccaacag tacagtactt tttctccaac gttcggccaa    300
gggacccagg tggacatcaa acga                                           324
```

<210> SEQ ID NO 15
<211> LENGTH: 348
<212> TYPE: DNA
<213> ORGANISM: Artificial Sequence
<220> FEATURE:
<223> OTHER INFORMATION: nucleotide sequence of VH of clone HSFN 68-27

<400> SEQUENCE: 15

```
caggtgcagc tggtggagtc cggggggaggc ctggtcaagc ctgggggtc ccggagactc      60 tcctgtgcag cctctggatt caccttcagt acctactaca tgagctgggt ccgccaggct    120
ccaggcaagg ggctagagtg gatcggatac attggtacta gtagtggtac cacttactac    180
gcgaactctg tgaagggccg attcaccatc tccagcgaca cgcccagaa ttccgtatat    240 ctgcaaatga acagtctgag acctgaggac acggccgtct attactgtgc aagagggctg    300
ggcagaatta acttgtgggg ccaaggcacc ctggtcaccg tctcctca                348
```

<210> SEQ ID NO 16
<211> LENGTH: 109
<212> TYPE: PRT
<213> ORGANISM: Artificial Sequence
<220> FEATURE:
<223> OTHER INFORMATION: amino acid sequence of VL of clone HSFN 68-41

<400> SEQUENCE: 16

```
Glu Leu Gln Met Thr Gln Ser Pro Ser Ser Val Ser Ala Ser Val Gly
  1               5                  10                  15

Asp Arg Val Thr Ile Ser Cys Arg Ala Ser Gln Asp Ile Arg Ser Leu
             20                  25                  30

Leu Ala Trp Tyr Gln Gln Lys Pro Gly Lys Ala Pro Lys Leu Leu Ile
         35                  40                  45

Tyr Lys Ala Ser Thr Leu Glu Ser Gly Val Pro Ser Arg Phe Ser Gly
     50                  55                  60

Ser Gly Ser Gly Thr Glu Phe Thr Leu Thr Ile Ser Asn Leu Gln Pro
 65                  70                  75                  80

Asp Asp Phe Ala Thr Tyr Tyr Cys Gln Gln Tyr Ser Arg Tyr Ser Gly
             85                  90                  95

Gly Thr Phe Gly Gln Gly Thr Lys Val Glu Ile Arg Arg
            100                 105
```

<210> SEQ ID NO 17
<211> LENGTH: 116
<212> TYPE: PRT
<213> ORGANISM: Artificial Sequence
<220> FEATURE:
<223> OTHER INFORMATION: amino acid sequence of VH of clone HSFN 68-41

<400> SEQUENCE: 17

```
Gln Gln Gln Leu Val Glu Ser Gly Gly Gly Leu Val Gln Pro Gly Gly
  1               5                  10                  15
```

Ser Leu Arg Leu Ser Cys Ala Ala Ser Gly Phe Thr Phe Ser Thr Tyr
            20                  25                  30

Tyr Met Ser Trp Val Arg Gln Ala Pro Gly Lys Gly Leu Glu Trp Val
        35                  40                  45

Gly Tyr Ile Gly Thr Ser Gly Thr Thr Tyr Tyr Ala Asn Ser Val
    50                  55                  60

Lys Gly Arg Phe Thr Ile Ser Ser Asp Asn Ala Lys Asn Ser Val Tyr
65                  70                  75                  80

Leu Gln Met Asn Ser Leu Arg Pro Glu Asp Thr Ala Val Tyr Tyr Cys
                85                  90                  95

Ala Arg Gly Leu Gly Arg Ile Asn Leu Trp Gly Gln Gly Thr Leu Val
            100                 105                 110

Thr Val Ser Ser
        115

<210> SEQ ID NO 18
<211> LENGTH: 327
<212> TYPE: DNA
<213> ORGANISM: Artificial Sequence
<220> FEATURE:
<223> OTHER INFORMATION: nucleotide sequence of VL of clone HSFN 68-41

<400> SEQUENCE: 18
gagctccaga tgacccagtc tccatcttct gtgtctgcat ctgtgggaga cagagtcacc      60
atctcttgtc gggcgagtca ggatattcgc agcttattag cctggtatca gcagaaacca    120
gggaaagccc ctaaactcct gatctataag gcgtctactt tagaaagtgg ggtcccatca    180
aggttcagcg gcagtggatc tgggacagaa ttcactctca ccatcagcaa cctgcagcct    240
gacgattttg caacttatta ctgccaacaa tatagtcgtt attcaggtgg gacgttcggc    300
caagggacca aggtggaaat cagacga                                        327

<210> SEQ ID NO 19
<211> LENGTH: 348
<212> TYPE: DNA
<213> ORGANISM: Artificial Sequence
<220> FEATURE:
<223> OTHER INFORMATION: nucleotide sequence of VH of clone HSFN 68-41

<400> SEQUENCE: 19
cagcagcagc tggtggagtc tgggggaggc ttggtacagc cggggggggtc cctgagactc     60 tcctgtgcag cctctggatt caccttcagt acctactaca tgagctgggt ccgccaggct   120
ccagggaagg ggctagagtg ggtcggatac attggtacta gtagtggtac cacttactac   180
gcgaactctg tgaagggccg attcaccatc tccagcgaca cgccaagaa ttccgtatat    240 ctgcaaatga acagtctgag acctgaggac acggccgtct attactgtgc aagagggctg   300
ggcagaatta acttgtgggg ccaaggcacc ctggtcaccg tctcctca                348

<210> SEQ ID NO 20
<211> LENGTH: 116
<212> TYPE: PRT
<213> ORGANISM: Artificial Sequence
<220> FEATURE:
<223> OTHER INFORMATION: amino acid sequence of VH of anti-HGF/SF
      rabbit/human chimeric monoclonal antibody SFN 68

<400> SEQUENCE: 20

Gln Gln Gln Leu Val Glu Ser Gly Gly Arg Leu Val Asn Pro Gly Glu
1               5                   10                  15

```
Ser Leu Thr Leu Thr Cys Lys Ala Ser Gly Phe Thr Phe Ser Thr Tyr
         20                  25                  30

Tyr Met Ser Trp Val Arg Gln Ala Pro Gly Lys Gly Leu Glu Trp Ile
         35                  40                  45

Gly Tyr Ile Gly Thr Ser Gly Thr Thr Tyr Tyr Ala Asn Ser Val
     50                  55                  60

Lys Gly Arg Phe Thr Ile Ser Ser Asp Asn Ala Gln Asn Thr Val Phe
 65                  70                  75                  80

Leu Gln Met Thr Ser Leu Thr Asp Ser Asp Thr Ala Thr Tyr Phe Cys
                 85                  90                  95

Ala Arg Gly Leu Gly Arg Ile Asn Leu Trp Gly Pro Gly Thr Leu Val
             100                 105                 110

Thr Val Ser Ser
        115

<210> SEQ ID NO 21
<211> LENGTH: 37
<212> TYPE: DNA
<213> ORGANISM: Artificial Sequence
<220> FEATURE:
<223> OTHER INFORMATION: forward primer for amplification of VL of
      anti-HGF/SF humanized antibody

<400> SEQUENCE: 21
gggcccaggc ggccgagctc cagatgaccc agtctcc                          37

<210> SEQ ID NO 22
<211> LENGTH: 37
<212> TYPE: DNA
<213> ORGANISM: Artificial Sequence
<220> FEATURE:
<223> OTHER INFORMATION: forward primer for amplification of VL of
      anti-HGF/SF humanized antibody

<400> SEQUENCE: 22
gggcccaggc ggccgagctc gtgatgacyc agtctcc                          37

<210> SEQ ID NO 23
<211> LENGTH: 37
<212> TYPE: DNA
<213> ORGANISM: Artificial Sequence
<220> FEATURE:
<223> OTHER INFORMATION: forward primer for amplification of VL of
      anti-HGF/SF humanized antibody

<400> SEQUENCE: 23
gggcccaggc ggccgagctc gtgwtgacrc agtctcc                          37

<210> SEQ ID NO 24
<211> LENGTH: 37
<212> TYPE: DNA
<213> ORGANISM: Artificial Sequence
<220> FEATURE:
<223> OTHER INFORMATION: forward primer for amplification of VL of
      anti-HGF/SF humanized antibody

<400> SEQUENCE: 24
gggcccaggc ggccgagctc acactcacgc agtctcc                          37

<210> SEQ ID NO 25
<211> LENGTH: 24
<212> TYPE: DNA
<213> ORGANISM: Artificial Sequence
<220> FEATURE:
```

```
<223> OTHER INFORMATION: reverse primer for amplification of VL of
      anti-HGF/SF humanized antibody

<400> SEQUENCE: 25
gaagacagat ggtgcagcca cagt                                           24

<210> SEQ ID NO 26
<211> LENGTH: 21
<212> TYPE: DNA
<213> ORGANISM: Artificial Sequence
<220> FEATURE:
<223> OTHER INFORMATION: forward primer for amplification of Ckappa of
      anti-HGF/SF humanized antibody

<400> SEQUENCE: 26
actgtggctg caccatctgt c                                              21

<210> SEQ ID NO 27
<211> LENGTH: 20
<212> TYPE: DNA
<213> ORGANISM: Artificial Sequence
<220> FEATURE:
<223> OTHER INFORMATION: reverse primer for amplification of Ckappa of
      anti-HGF/SF humanized antibody, and reverse primer for assembly of
      VL and Ckappa PCR products

<400> SEQUENCE: 27
gccatggctg gttgggcagc                                                20

<210> SEQ ID NO 28
<211> LENGTH: 41
<212> TYPE: DNA
<213> ORGANISM: Artificial Sequence
<220> FEATURE:
<223> OTHER INFORMATION: forward primer for assembly of VL and Ckappa
      PCR products, and forward primer for assembly of light chain and
      heavy chain PCR products

<400> SEQUENCE: 28
gaggaggagg aggaggaggc ggggcccagg cggccgagct c                        41

<210> SEQ ID NO 29
<211> LENGTH: 41
<212> TYPE: DNA
<213> ORGANISM: Artificial Sequence
<220> FEATURE:
<223> OTHER INFORMATION: forward primer for amplification of heavy chain
      FR1 of anti-HGF/SF humanized antibody, forward primer for assembly
      of FR1 and FR2 PCR products, and forward primer for assembly of
      (FR1 and FR2) and FR3 PCR products

<400> SEQUENCE: 29
gctgcccaac cagccatggc ccaggtgcag ctggtggagt c                        41

<210> SEQ ID NO 30
<211> LENGTH: 41
<212> TYPE: DNA
<213> ORGANISM: Artificial Sequence
<220> FEATURE:
<223> OTHER INFORMATION: forward primer for amplification of heavy chain
      FR1 of anti-HGF/SF humanized antibody, forward primer for assembly
      of FR1 and FR2 PCR products, and forward primer for assembly of
      (FR1 and FR2) and FR3 PCR products

<400> SEQUENCE: 30
gctgcccaac cagccatggc ccagcagcag ctggtggagt c                        41
```

<210> SEQ ID NO 31
<211> LENGTH: 42
<212> TYPE: DNA
<213> ORGANISM: Artificial Sequence
<220> FEATURE:
<223> OTHER INFORMATION: reverse primer for amplification of heavy chain
      FR1 of anti-HGF/SF humanized antibody

<400> SEQUENCE: 31
gctcatgtag taggtactga aggtgaatcc agaggctgca ca                         42

<210> SEQ ID NO 32
<211> LENGTH: 65
<212> TYPE: DNA
<213> ORGANISM: Artificial Sequence
<220> FEATURE:
<223> OTHER INFORMATION: forward primer for amplification of heavy chain
      FR2 of anti-HGF/SF humanized antibody

<400> SEQUENCE: 32
cacagagttc gcgtagtaag tggtaccact actagtacca atgtatccga yccactctag      60
cccct                                                                 65

<210> SEQ ID NO 33
<211> LENGTH: 41
<212> TYPE: DNA
<213> ORGANISM: Artificial Sequence
<220> FEATURE:
<223> OTHER INFORMATION: reverse primer for amplification of heavy chain
      FR2 of anti-HGF/SF humanized antibody, and reverse primer for
      assembly of FR1 and FR2 PCR products

<400> SEQUENCE: 33
ttcagtacct actacatgag ctggrtccgc caggctccag g                         41

<210> SEQ ID NO 34
<211> LENGTH: 65
<212> TYPE: DNA
<213> ORGANISM: Artificial Sequence
<220> FEATURE:
<223> OTHER INFORMATION: reverse primer for amplification of heavy chain
      FR2 of anti-HGF/SF humanized antibody, and reverse primer for
      assembly of FR1 and FR2 PCR products

<400> SEQUENCE: 34
cacagagttc gcgtagtaag tggtaccact actagtacca atgtatgaga yccactctag      60
cccct                                                                 65

<210> SEQ ID NO 35
<211> LENGTH: 65
<212> TYPE: DNA
<213> ORGANISM: Artificial Sequence
<220> FEATURE:
<223> OTHER INFORMATION: forward primer for amplification of heavy chain
      FR3 of anti-HGF/SF humanized antibody

<400> SEQUENCE: 35
cttactacgc gaactctgtg aagggccgat tcaccatctc cagsgacaac gccmagaatt      60 ccsta                                                                 65

<210> SEQ ID NO 36
<211> LENGTH: 41
<212> TYPE: DNA
<213> ORGANISM: Artificial Sequence
<220> FEATURE:
<223> OTHER INFORMATION: reverse primer for amplification of heavy chain

```
                        FR3 of anti-HGF/SF humanized antibody, and reverse primer for
                        assembly of (FR1 and FR2) and FR3 PCR products

<400> SEQUENCE: 36
caagttaatt ctgcccagcc ctcttgcaca gtaatagacg g                                 41

<210> SEQ ID NO 37
<211> LENGTH: 42
<212> TYPE: DNA
<213> ORGANISM: Artificial Sequence
<220> FEATURE:
<223> OTHER INFORMATION: forward primer for amplification of heavy chain
                        FR4 of anti-HGF/SF humanized antibody

<400> SEQUENCE: 37
gggctgggca gaattaactt gtggggccaa ggcaccctgg tc                                42

<210> SEQ ID NO 38
<211> LENGTH: 21
<212> TYPE: DNA
<213> ORGANISM: Artificial Sequence
<220> FEATURE:
<223> OTHER INFORMATION: reverse primer for amplification of heavy chain
                        FR4 of anti-HGF/SF humanized antibody, and reverse primer for
                        assembly of (FR1, FR2 and FR3) and FR4 PCR products

<400> SEQUENCE: 38
agaagcgtag tccggaacgt c                                                      21

<210> SEQ ID NO 39
<211> LENGTH: 21
<212> TYPE: DNA
<213> ORGANISM: Artificial Sequence
<220> FEATURE:
<223> OTHER INFORMATION: forward primer for assembly of (FR1, FR2 and
                        FR3) and FR4 PCR products

<400> SEQUENCE: 39
gctgcccaac cagccatggc c                                                      21

<210> SEQ ID NO 40
<211> LENGTH: 39
<212> TYPE: DNA
<213> ORGANISM: Artificial Sequence
<220> FEATURE:
<223> OTHER INFORMATION: reverse primer for assembly of light chain and
                        heavy chain PCR products

<400> SEQUENCE: 40
gaggaggagg aggaggagag aagcgtagtc cggaacgtc                                   39
```

US 7,718,174 B2

ANTI-HGF/SF HUMANIZED ANTIBODY

FIELD OF THE INVENTION

The present invention relates to an anti-HGF/SF humanized antibody and a method for the preparation thereof. Specifically, the present invention relates to an anti-HGF/SF humanized antibody prepared by displaying on the surface of a phage an anti-HGF/SF chimeric Fab library comprising a set of a human antibody light chain variable region ($V_L$) and a human antibody heavy chain variable region ($V_H$) which are grafted with heavy chain complementary determining regions (HCDRs) of an anti-HGF/SF antibody of an animal other than human.

BACKGROUND OF THE INVENTION

HGF/SF (hepatocyte growth factor/scatter factor) is a multifunctional heterodimeric polypeptide produced by mesenchymal cells, and it is composed of an alpha-chain containing an N-terminal domain and four kringle domains (NK4) covalently linked to a serine protease-like beta-chain C-terminal domain. Further, human HGF/SF is produced in the form of a biologically inactive single chain precursor consisting of 728 amino acids, and biologically active HGF/SF is generated therefrom through cleavage at the R494 residue by a specific serum serine protease. The active form of HGF/SF is a disulfide-linked heterodimer composed of a 69 kDa alpha-chain and a 34 kDa beta-chain.

The binding of HGF/SF to its receptor, CMET, induces the growth of various cell types, mediates the epithelial mesenchymal transitions and the formation of tubules and lumens, and promotes angiogenesis. A cMET and HGF/SF knockout mouse is not often embryonically viable and shows developmental defects in placenta, fetal liver and limb/muscle formation (Cao et al., *PNAS* 98 (13): 7443-7448, 2001; Gmyrek et al., *American Journal of Pathology* 159 (2): 579-590, 2001). Further, cMET was reported to be over-expressed in various human cancers of the liver, prostate, colon, breast, brain and skin (Maulik et al, *Cytokine & Growth Factor Reviews,* 13(1), 41-59,200). cMET activation markedly enhances the metastastic spread of cancer because of its stimulatory influences on the processes e.g., angiogenesis, cell motility, and cell surface protease regulation, and therefore, cMET has been regarded as an important target factor for the prevention and treatment of cancer (Wielenga et al., *American Journal of Pathology* 157 (5): 1563-1573, 2000).

Monoclonal antibodies (mAbs) have enormous potential as therapeutic agents. However, non-human antibodies are highly immunogenic in the human body and their short serum half life severely limits their clinical efficacy. To circumvent such a problem, a "humanized antibody" has been constructed by grafting complementarity-determining regions (CDRs) of the parent mAb variable region that directly binds to antigens onto a human antibody framework. (CDR-grafting method). The humanized antibody thus obtained reduces the immunogenicity in human, and prolongs the serum half-life in human while keeping the binding affinity and specificity of the parent antibody (Baselga, J. et al., *J Clin Oncol,* 14, 737-744, 1996).

However, the simple CDR-grafting method often yields humanized antibodies which bind to their antigens much more weakly than the parent mAb (Carter, P. et al., *Proc Natl Acad Sci USA,* 89, 4285-4428, 1992; Eigenbrot, C. et al., *Proteins,* 18, 49-62, 1994; and Kettleborough, C. A. et al., *Protein Eng.,* 4, 773-778, 1991)

To provide a humanized antibody which preserves the original affinity of the parent mAb, the key residues in the framework regions (FRs) of the human antibody essential for forming a CDR loop were replaced with the corresponding amino acid residues from the parent mAb (Chothia, C. et al., *Nature,* 342, 877-888, 1989). But, the identification of such framework residues that affect antigen binding has proved to be unduly time-consuming.

The present inventors sought to develop an anti-HGF/SF humanized antibody having the equal or greater binding activity than that of the parent antibody with reduced immunogenicity in human.

SUMMARY OF THE INVENTION

Accordingly, it is an object of the present invention to provide an anti-HGF/SF humanized antibody having the reduced immunogenicity in human and the binding affinity equal or greater than that of the parent monoclonal antibody.

It is another object of the present invention to provide a method for preparing the anti-HGF/SF humanized antibody by using a process of phage display.

It is another object of the present invention to provide a

In accordance with one aspect of the present invention, there is provided an anti-HGF/SF humanized antibody comprising:

a) a human antibody heavy chain variable region ($V_H$) having the following amino acid sequences at complementary determining regions (CDRs):

TYYMS YIGTSSGTTYYANSVKG GLGRINL (SEQ ID NOs: 1 to 3);

b) a light chain variable region ($V_L$) identical to the human antibody $V_L$;

c) a heavy chain constant region identical to the human antibody heavy chain constant region; and d) a light chain constant region identical to the human antibody light chain constant region.

In accordance with another aspect of the present invention, there is provided a method for preparing the anti-HGF/SF humanized antibody comprising the steps of: 1) preparing a chimeric Fab library composed of a set of the human antibody $V_L$ and $V_H$ of having the amino acid sequences of SEQ ID NOs: 1 to 3 at CDRs, and 2) displaying the Fab library on the surface of a phage.

In accordance with another aspect of the present invention, there is provided a pharmaceutical composition for preventing or treating cancer comprising the humanized antibody together with a pharmaceutically acceptable carrier.

In accordance with another aspect of the present invention, there is provided a method of the anti-HGF/SF humanized antibody for preventing and treating cancer.

BRIEF DESCRIPTION OF DRAWINGS

The above and other objects and features of the present invention will become apparent from the following description of the invention taken in conjunction with the following accompanying drawings, which respectively show:

FIGS. 2 and 3: amino acid sequences of $V_L$ and $V_H$ of the parent rabbit/human chimeric monoclonal antibody SFN 68 (SEQ ID NO: 20) and the inventive humanized antibody, respectively (-: identical amino acids, bold type: amino acids substituted by PCR primers, underline: a primer sequences, and, *: diversified region cloned from human cDNA by PCR), wherein, in FIG. 2, the number 13 ($V_L$ of HSFN 68-13 clone) is SEQ ID NO: 4, number 16 ($V_L$ HSFN 68-16 clone) is SEQ ID NO: 8, number 27 ($V_L$ of HSFN 68-27 clone) is SEQ ID NO: 12; and number 41 ($V_L$ HSFN 68-41 clone) is SEQ ID NO: 16; and in FIG. 3, the number 13 ($V_H$ of HSFN 68-13 clone) is SEQ ID NO: 5, number 16 ($V_H$ HSFN 68-16 clone) is SEQ ID NO: 9, number 27 ($V_H$ of HSFN 68-27 clone) is SEQ ID NO: 13; and number 41 ($V_H$ HSFN 68-41 clone) is SEQ ID NO: 17.

DETAILED DESCRIPTION OF THE INVENTION

Figure 1:
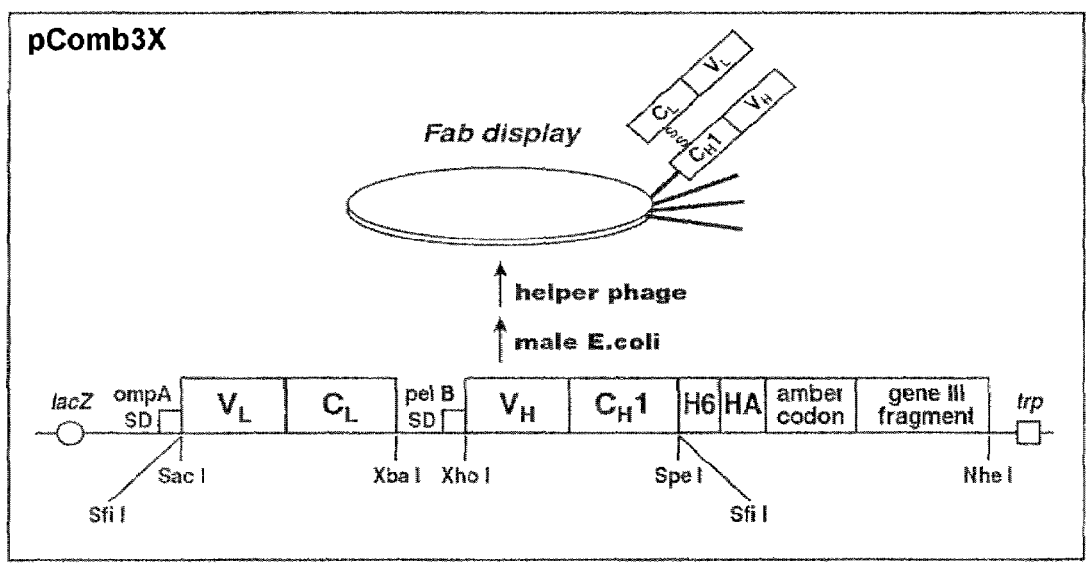
FIG. 1: the genetic map of phagemid vector pComb3X used for antibody library construction while displaying Fab on the surface of a phage.

In the present invention, a chimeric antibody is an antibody whose antibody variable region or complementary determining region (CDR) is derived from an animal different from the animal source of the other portion of the antibody. For example, the chimeric antibody variable region is derived from an animal excluding human (e.g. mouse, rabbit and poultry) and the chimeric antibody constant region is derived from human. This chimeric antibody can be prepared by any one of the conventional methods such as genetic recombination.

A humanized antibody refers to an antibody prepared by grafting CDRs of a non-human derived monoclonal antibody onto human derived antibody to reduce the immunogenicity in human while maintaining the high affinity and specificity of the non-human derived monoclonal antibody.

A heavy chain refers to a full length heavy chain comprising: a variable region domain $V_H$, which comprises amino acid sequences having enough variable region sequences to allow the specificity to an antigen, and 3 constant region domains, $C_H1$, $C_H2$; and $C_H3$, and fragments thereof.

A light chain refers to a full length light chain comprising: a variable region domain $V_L$, which comprises amino acid sequences having enough variable region sequences to allow the specificity to an antigen, and a constant region domain, $C_L$, and fragments thereof.

Further, Fab is composed of light chain and heavy chain variable regions, a light chain constant region, and the first constant region of heavy chain ($C_H1$), and has 1 epitope.

The inventive humanized antibody is composed of human antibody $V_L$, human antibody $V_H$ grafted with HCDRs of anti-HGF/SF antibody derived from an animal other than human, and human antibody heavy chain and light chain constant regions.

The HCDRs grafted onto the heavy chain variable region can be derived from any antibody heavy chain of any animal other than human having amino acid sequences of SEQ ID NOs: 1 to 3, and it is preferable that the HCDRs are derived from $V_H$ of anti-HGF/SF rabbit/human chimeric monoclonal antibody SFN 68 having an amino acid sequence of SEQ ID NO: 20 (Korea patent No. 10-0556660).

The inventive anti-HGF/SF humanized antibody can be in the form of a whole antibody or a fragment thereof, preferable Fab.

Further, the inventive humanized antibody has a binding affinity ($K_D$) ranging from $1 \times 10^{-9}$ to $5 \times 10^{-8}$ M.

In order to enhance the binding affinity of the inventive humanized antibody to the antigen, the present invention may comprise a human antibody $V_H$ further grafted with amino acid residues of the framework regions influencing the conformation of CDR loop of the parent antibody, and it is preferable that the amino acid residues are one or more amino acid residues selected from the group consisting of the $2^{nd}$, $37^{th}$, $48^{th}$, $49^{th}$, $71^{st}$, $75^{th}$ and $78^{th}$ amino acid residues of SFN 68 $V_H$ having the amino acid sequence of SEQ ID NO: 20. In the present invention, the number of amino acid residue is assigned by Kabat numbering scheme.

The anti-HGF/SF humanized antibody of the present invention can be prepared as follows.

First, total RNA is extracted from human bone marrow and subjected to cDNA synthesis. A human antibody $V_L$ synthesized by PCR using the cDNA as thus obtained a template and one of the degenerate primer combinations, and the human antibody light chain constant regions (Cκ) are fused by overlap extension PCR to obtain a light chain gene.

In order to amplify human antibody $V_H$ grafted with HCDRs having the amino acid sequences of SEQ ID NOs: 1 to 3, e.g., HCDRs of the rabbit/human chimeric monoclonal antibody SFN 68, framework regions FR1 (including HCDR1), FR2 (including HCDR2), FR3 (including HCDR3) and FR4 (including human antibody heavy chain constant region $C_H1$) are synthesized by PCR using primers designed to allow grafting of HCDR1 (a.a. 31-35), HCDR2 (a.a. 50-65) or HCDR3 (a.a. 95-102) of SFN 68 $V_H$ having the amino acid sequence of SEQ ID NO: 20.

At this time, the primers may be designed to allow further grafting of any amino acid residues of SFN 68 onto the corresponding positions of FRs of a human antibody to enhance the binding affinity of the resulting antibody to an antigen. Such additionally graftable amino acid residues can be determined by: aligning the amino acid sequences of the heavy chain of antibody SFN 68 and that of a human antibody having high homology therewith, and identifying the FR amino acid residues, which influence on the conformation of CDR loop, based on the difference of amino acid residues between the two aligned amino acid sequences. The amino acid residues are preferably one or more amino acid residues selected from the group consisting of the $2^{nd}$, $37^{th}$, $48^{th}$, $49^{th}$, $71^{st}$, $75^{th}$ and $78^{th}$ amino acid residue of SFN 68 $V_H$ having the amino acid sequence of SEQ ID NO: 20.

The obtained PCR products for FR1 to FR4 are fused by overlap extension PCR to prepare a heavy chain gene composed of: a human antibody $V_H$ grafted with HCDRs of the rabbit/human chimeric monoclonal antibody SFN 68 and a human antibody heavy chain constant region ($C_H1$). The primers used in this process are designed to comprise 20 or more bases corresponding to each HCDR for effective fusion of the PCR products.

In the present invention, a DNA library of the rabbit/human chimeric Fab antibody is prepared by fusing the obtained heavy chain and light chain genes by overlap extension PCR.

In the present invention, a rabbit/human chimeric Fab antibody library is prepared by cloning the DNA fragments of the DNA library into a vector, and transforming the resulting vector into a host cell, e.g., E. coli strain. Any vectors and E. coli strains conventionally used in the art may be used in the present invention without any limitation, while it is preferable to use a phagemid vector, e.g., pComb3X (the Scripps Research Institute, CA, USA) and E. coli ER2537 (NEB). When E. coli strains are transformed with the phagemid vector containing a library DNA, the introduced phage displayed Fab antibody as a fusion protein with the phage coat protein-pIII.

Thereafter, phage clones containing anti-HGF/SF Fab are selected by enzyme immunoassay using an ELISA plate coated with HGF/SF and anti-human goat Fab polyclonal antibody. Among the selected phage clones containing anti-HGF/SF Fab, the clones showing the equal or greater binding affinity to HGF/SF than that of SFN 68 were named as HSFN 68-13, HSFN 68-16, HSFN 68-27 and HSFN 68-41, respectively.

The above-mentioned HSFN 68-13 clone encodes $V_L$ and $V_H$ having the nucleotide sequences of SEQ ID NOs: 6 and 7, respectively; HSFN 68-16 clone, $V_L$ and $V_H$ having the nucleotide sequences of SEQ ID NOs: 10 and 11, respectively; HSFN 68-27 clone, $V_L$ and $V_H$ having the nucleotide sequences of SEQ ID NOs: 14 and 15, respectively; and HSFN 68-41 clone, $V_L$ and $V_H$ having the nucleotide sequences of SEQ ID NOs: 18 and 19, respectively.

The amino acid sequences of the Fab clones are deduced from the analyzed nucleotide sequences, respectively. $V_L$ and $V_H$ of HSFN 68-13 clone have the amino acid sequences of SEQ ID NOs: 4 and 5, respectively; $V_L$ and $V_H$ of HSFN 68-16 clone, the amino acid sequences of SEQ ID NOs: 8 and 9, respectively; $V_L$ and $V_H$ of HSFN 68-27 clone, the amino acid sequences of SEQ ID NOs: 12 and 13, respectively; and $V_L$ and $V_H$ of HSFN 68-41 clone, the amino acid sequences of SEQ ID NOs: 16 and 17, respectively.

Figure 3:
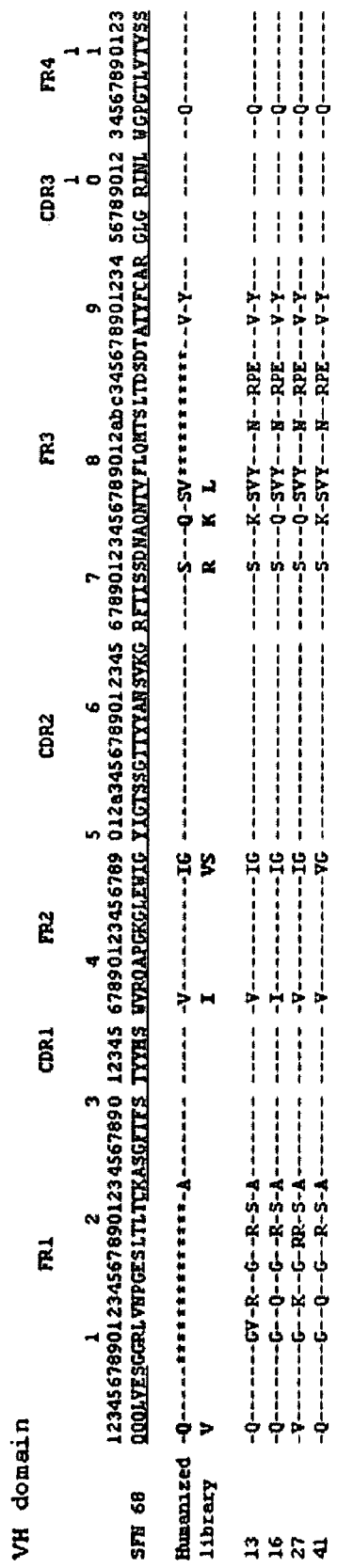

Analyses of FRs and CDRs in the amino acid sequences of the clones reveal that $V_L$ and $V_H$ of the clones have 4 FRs and 3 CDRs, respectively (FIGS. 2 and 3). Further, the sequence homology between the light chains of HSFN 68 clones and SFN 68 Fab range from 78 to 81%, while that between the heavy chains range from 85 to 90%.

The heavy chain and light chain of the inventive humanized antibody may be coded by genes comprising the nucleotide sequences expected from the humanized antibody heavy chain and light chain in consideration of the genetic codes. It is well-known that there are several different codons encoding an amino acid due to the degeneracy of codons. Therefore, the present invention includes all possible nucleotide sequences expected from the amino acid sequences of the humanized antibody heavy chain and light chain. Preferably, the sequences of heavy chain and light chain genes of the humanized antibody include one or more codons preferred in the chosen host cell.

Further, in the present invention, phagemid DNAs of the selected clones are transformed into *E. coli* strain to express an antibody protein, and the culture solution containing the produced antibody is purified in accordance with any one of the conventional methods to obtain anti-HGF/SF humanized antibody. Any *E. coli* strain and purification method conventionally used in the art for producing a recombinant protein may be used in the present invention without any limitation, while it is preferable to use HB2151 (Amersham Pharmacia Biotech) and a method comprising the steps of concentrating the obtained culture solution and subjecting the concentrate to the protein L column (Pierce Chemical Co, USA) as a purification method.

Examination of the affinities of the HSFN 68 clones to HGF/SF revealed that HSFN68-13 clone possesses the highest affinity out of the four clones tested, and this is about 6-fold higher than that of SFN68. HSFN68-16 shows the lowest affinity and clones HSFN68-27 and HSFN68-41 exhibit equal affinities to that of SFN 68 (Table 2).

Figure 5:
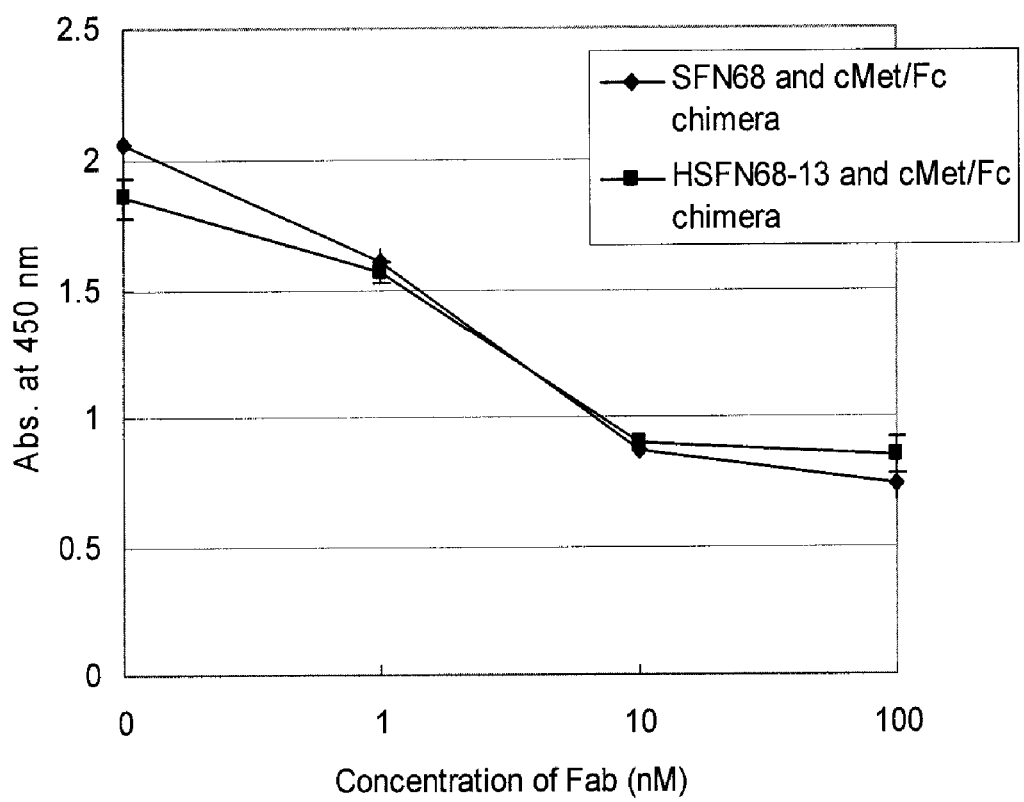
FIG. 5: the extent of inhibition of the binding of HGF/SF to cMET/Fc chimera by the inventive humanized antibody relative to that of the parent antibody SFN 68.
Figure 6:
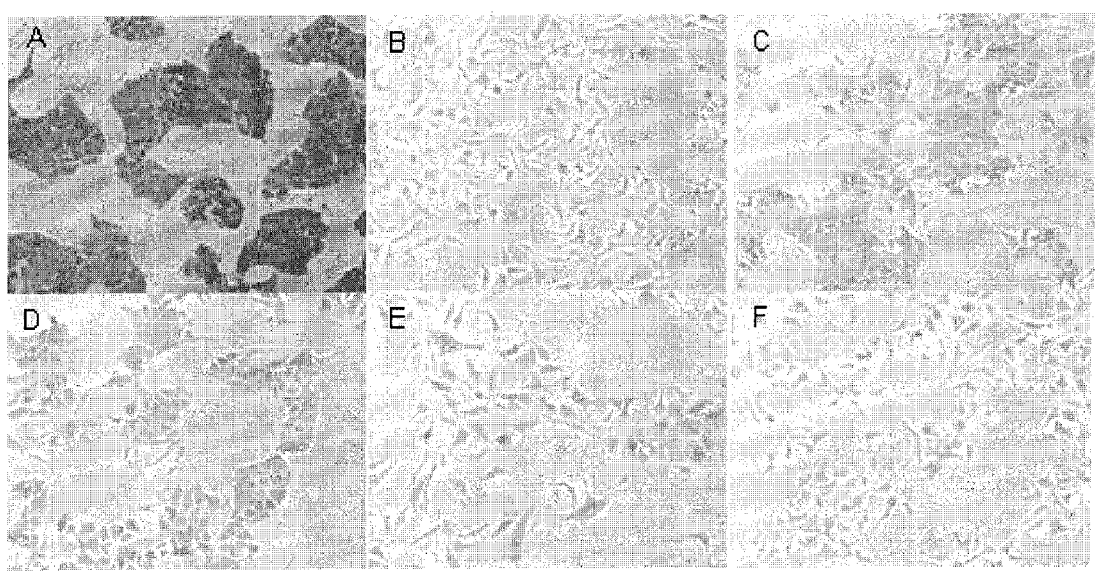
FIG. 6A-F: MDCK scattering inhibition effects of a mixture of the inventive humanized antibody and anti-human Fab specific IgG against HGF/SF.

Further, the inventive humanized antibody inhibits the binding of HGF/SF to cMET/Fc chimera in the level comparable to that of SFN 68 (FIG. 5), and exhibits the equal neutralizing activity to that of SFN 68 (FIG. 6).

Thus, the inventive humanized antibody comprising human $V_L$, and humanized $V_H$ comprising grafted HCDRs and some residues of FRs, has the equal or greater binding affinity to HGF/SF than the parent SFN 68, the neutralizing activity inhibiting the binding of HGF/SF to the receptor thereof, cMET, and the reduced immunogenicity in human. Therefore, the humanized antibody can be used for an effective medicament for preventing or treating diseases caused by the binding of HGF to a receptor thereof, cMET, such as a cancer.

Accordingly, the present invention further provides a pharmaceutical composition for preventing or treating a cancer comprising the humanized antibody as an active ingredient. The inventive pharmaceutical composition may comprise a pharmaceutically acceptable carrier, and formulated in accordance with any one of the conventional methods.

The pharmaceutical composition of the present invention can be administered by injection (e.g., intramuscular, intravenous, intraperitoneal, subcutaneous), or by other methods such as infusion that ensure its delivery to the bloodstream in an effective form. It should be understood that the amount of the active ingredient actually administered ought to be determined in light of various relevant factors including the condition to be treated, the chosen route of administration, the age, sex and body weight of the individual patient, and the severity of the patient's symptom; and, therefore, the above dose should not be intended to limit the scope of the invention in any way.

Further, the present invention provides a method for preventing and treating diseases by using the humanized antibody. Preferably, the disease includes, but is not limited to, various cancers of liver, prostate, colon, breast, brain and skin, and malaria, Alzheimer's disease and so on.

The following Examples are intended to further illustrate the present invention without limiting its scope.

Example 1

Phage Library Construction Comprising HGF/SF Rabbit/Human Chimeric Fab (1-1) Amplification of a Human Antibody Light Chain Variable Region ($V_L$)

Total RNA of human bone marrow (donated from a laboratory researcher) was extracted with the use of TRI reagent (Molecular Research Center, USA), and purified by the method of lithium chloride precipitation. Human cDNA was synthesized by using the SUPERSCRIPT Preamplification System with oligo (dT) priming (Life Technologies, Inc.).

In order to amplify human antibody $V_L$, PCR was performed using the obtained human cDNA as a template and one of the degenerate primer combinations of SEQ ID NOs: 21 to 25, as described in Table 1.

TABLE 1

| Antibody Variable region | Forward primer | Reverse primer |
|---|---|---|
| $V_L$ | SEQ ID NO: 21 | SEQ ID NO: 25 |
| | SEQ ID NO: 22 | SEQ ID NO: 25 |
| | SEQ ID NO: 23 | SEQ ID NO: 25 |
| | SEQ ID NO: 24 | SEQ ID NO: 25 |

W = A or T, R = A or G, and Y = C or T

A PCR reaction solution was prepared by mixing 1 µl of the obtained cDNA (about 0.5 µg), 60 pmol each the primers, 10 µl of 10×PCR buffer, 8 µl of 2.5 mM dNTP mixture and 0.5 µl of Taq polymerase, and the resulting mixture was adjusted to a final volume of 100 µl with distilled water. The PCR condition was 30 cycles of 15 sec at 94° C., 30 sec at 56° C. and 90 sec at 72° C., and 10 min of final extension at 72° C.

The amplified DNA was subjected to 1% agarose gel electrophoresis and purified from the gel using LaboPass gel extraction kit (Cosmo, Korea).

(1-2) Amplification of a Human Antibody Light Chain Constant Region (Cκ)

In order to amplify a human antibody light chain constant region (Cκ), PCR was conducted by repeating the procedure of (1-1) except for using 20 ng of vector pComb3XTT (Scripps Research Institute, USA) containing human Fab Cκ sequence as a template, together with 60 pmol of each primer (SEQ ID NOs: 26 and 27).

(1-3) Amplification of a Light Chain

Overlap extension PCR was conducted to prepare a light chain gene part by connecting the human antibody $V_L$ of (1-1) to human antibody Cκ of (1-2).

A PCR reaction solution was prepared by mixing 100 ng each of the $V_L$ and Cκ PCR product, 60 pmol each of primers (SEQ ID NOs: 28 and 27), 10 μl of 10×PCR buffer, 8 μl of 2.5 mM dNTP mixture and 0.5 μl of Taq polymerase, and the mixture just obtained was adjusted to a final volume of 100 μl with distilled water. The PCR condition employed was 15 cycles of 15 sec at 94° C., 30 sec at 56° C. and 2 min at 72° C., and 10 min of final extension at 72° C. The amplified DNA was subjected to agarose gel electrophoresis and purified in accordance with the procedure of (1-1).

(1-4) Amplification of a SFN 68 HCDR Grafted Heavy Chain Variable Region ($V_H$) and a Human Antibody Heavy Chain Constant Region ($C_H1$)

PCR was conducted by using the human cDNA of (1-1) as a template, and primers (SEQ ID NOs: 29 to 36) described in Table 2 to amplify the human antibody heavy chain framework region FR1 (including HCDR1), FR2 (including HCDR2) and FR3 (including HCDR3), which were grafted with the HCDRs of the rabbit/human chimeric monoclonal antibody SFN 68 (Korea patent No. 10-0556660), and an additional PCR was conducted by using pComb3XTT expression vector (the Scripps Research Institute, USA) containing human Fab $C_H1$ sequence as a template, and primers (SEQ ID NOs: and 38) described in Table 2 to amplify FR 4 which includes human antibody CHI sequence.

The PCRs were conducted by repeating the procedure of (1-1) except for using 500 ng of cDNA and 20 ng of pComb3XTT expression vector as a template, respectively, and the amplified DNA was subjected to agarose gel electrophoresis and purified in accordance with the procedure of (1-1).

TABLE 2

| Antibody Variable region | | Forward primer | Reverse primer |
|---|---|---|---|
| $V_H$ | FR1 | SEQ ID NO: 29 | SEQ ID NO: 31 |
| | FR1 | SEQ ID NO: 30 | SEQ ID NO: 31 |
| | FR2 | SEQ ID NO: 32 | SEQ ID NO: 33 |
| | FR2 | SEQ ID NO: 32 | SEQ ID NO: 34 |
| | FR3 | SEQ ID NO: 35 | SEQ ID NO: 36 |
| | FR4 | SEQ ID NO: 37 | SEQ ID NO: 38 |

As shown in FIG. 3, the respective primer pairs were designed to allow grafting HCDR1 (a.a. 31-35), HCDR2 (a.a. 50-65) or HCDR3 (a.a. 95-102), and one or more amino acid residues selected from the group consisting of the $2^{nd}$, $37^{th}$, $48^{th}$, $49^{th}$, $71^{st}$, $75^{th}$ and $78^{th}$ amino acid residues of SFN 68 $V_H$ having the amino acid sequence of SEQ ID NO: 20 onto the corresponding human antibody heavy chain sequences.

(1-5) Amplification of a Heavy Chain

Overlap extension PCR was conducted by repeating the procedure of (1-3) except for using the template and the pairs of primers described in Table 3 to synthesize a heavy chain comprising SFN 68 HCDR grafted $V_H$ and human CHI by fusing the PCR products of (1-4) for FR1 to FR4, sequentially. The amplified DNA was subjected to agarose gel electrophoresis and purified in accordance with the procedure of (1-1).

The primers used were designed to have 20 and more nucleotide sequences corresponding to HCDR nucleotide sequences of the nucleotide sequences encoding anti-HGF/SF Fab for effective fusion.

TABLE 3

| Template | Forward primer | Reverse primer |
|---|---|---|
| FR1 and FR2 | SEQ ID NO: 29 | SEQ ID NO: 33 |
| | SEQ ID NO: 29 | SEQ ID NO: 34 |
| | SEQ ID NO: 30 | SEQ ID NO: 33 |
| | SEQ ID NO: 30 | SEQ ID NO: 34 |
| (FR1 + FR2) and FR3 | SEQ ID NO: 29 | SEQ ID NO: 36 |
| | SEQ ID NO: 30 | SEQ ID NO: 36 |
| (FR1 + FR2 + FR3) and FR4 | SEQ ID NO: 39 | SEQ ID NO: 38 |

(1-6) Preparation of Anti-HGF/SF Rabbit/Human Chimeric Fab Library

PCR was conducted by repeating the procedure of (1-3) except for using 100 ng each of the purified light chain and heavy chain gene products of (1-3) or (1-5) as a template, and 60 pmol each of primers (SEQ ID NOs: 28 and 40) to prepare an anti-HGF/SF rabbit/human chimeric Fab library gene. The amplified DNA was subjected to agarose gel electrophoresis and purified in accordance with the procedure of (1-1).

(1-7) Preparation of a Phage Containing the Anti-HGF/SF Rabbit/Human Chimeric Fab Library The purified chimeric Fab library obtained in (1-6) was subjected to SfiI (Roche, USA) digestion, isolated and cloned into a phagemid vector pComb3X (Scripps Research Institute, CA, USA) (FIG. 1). The phagemid DNA thus obtained was transformed into E. coli strain ER2537 (NEB, USA) by electrophoration.

The introduced phage displayed Fab as a fusion protein with the phage coat protein pIII.

The transformed bacteria were incubated at 37° C., 250 rpm using SB medium (including 10 g of MOPS (3(N-Morpholino) propanesulfonic acid, Sigma), 30 g of tryptone (BD Biosciences, Difco) and 20 g of yeast extract (BD sciences, Difco)), phage particles were rescued by adding helper phage VCSM13 (Stratagene, USA) to the culture solution (see Barbas, C. F. et al., *Phage Display: A Laboratory Manual*. Cold Spring Harbor Laboratory Press, Cold Spring Harbor, N.Y., 2001). After overnight incubation, the cell pellets thus obtained were removed by centrifugation at 4° C., 14,000×g for 20 min, and then the phages were precipitated by adding 4% (w/v) polyethylene glycol-8000 (PEG, Sigma) and 3% (w/v) NaCl to the supernatant, and the phages were incubated on ice for 30 min. The resulting phages were subjected to centrifugation at 4° C., 17,000×g for 20 min, and the obtained pellets were dissolved in 1 ml of TBS containing 3% (w/v) BSA (bovine serum albumin) (TBSB). The diversity of the library thus obtained was confirmed by phage titration and BstNI fingerprinting (see Barbas, C. F. et al., supra).

Example 2

Selection of a Phage Clone Containing the Humanized Anti-HGF/SF Fab (2-1) Biopanning Each well of a 96-well plate (costar, USA) was coated at 4° C. overnight with 50 µl of 10 µg/ml solution of HGF/SF dissolved in 0.1 M sodium bicarbonate buffer (pH 8.6, coating buffer). The uncoated portion was blocked by adding 100 µl/well of TBSB including 5% BSA at 37° C. for 2 hours. 50 µl of a solution containing Fab-displaying phage of Example 1 suspended in TBSB was added to each well. The plate was kept at 37° C. for 2 hrs, and washed with TBS containing 0.05% Tween 20 (TBS-T). The phages fixed in the wells were eluted with 100 µl of 0.1M HCl-glycine (pH 2.2), and neutralized with 16 µl of 1 M Tris-Cl (pH 9.1). 4 rounds of the pannings were carried out, and the washing steps were increased from once in the first round to 5 times in the second and the third rounds, respectively, and 10 times in the fourth round. The eluted phages in each round of the pannings were infected to exponentially growing ER2537 cells. The phages were rescued in accordance with the method described in (1-7) of Example 1, and the input and output titer of the phages was monitored as described in Barbas, C. F. et al., supra.

(2-2) ELISA

In order to find out the clones binding to HGF/SF, an ELISA was carried out by using a surface displayed Fab, as follows.

Specifically, after the last round of panning of (2-1), 41 clones were randomly selected from the output titer plate, inoculated to SB medium containing carbenicillin, incubated 4 hours, and phages were rescued with helper phage VCSM13. After 2 hours, kanamycin was added to each well, and incubated overnight to obtain supernatants containing phages displaying Fab on their surfaces. Each well of a 96-well ELISA plate was coated with 1 µg/ml HGF/SF dissolved in the coating buffer at 4° C. overnight and blocked with TBSB. 50 µl of the obtained phage supernatants premixed with the equal volume of TBSB were transferred to the coated wells, and the plate was incubated at 37° C. for 1 hour and washed with TBS-T. Bound phages were detected with horseradish peroxidase (HRP)-conjugated sheep anti-M13 phage polyclonal antibodies (Amersham Pharmacia Biotech) using ABTS (One-step ABTS solution, Sigma) as a substrate. After 30 min incubation at 37° C., optical densities of the wells were measured at 405 nm.

As a result, 33 clones showing a binding activity to HGF/SF were selected. ELISA was repeated for the selected clones as described above, and four clones showing the equal or greater binding affinities to HGF/SF than that of SFN 68 were selected. These four clones were named as HSFN 68-13, 16, 27 and 41, respectively, and used for further experiments.

Example 3

Nucleotide Sequencing of Selected Phage Clones

The Fab genes of the 4 clones selected in Example 2 were sequenced by the dideoxy chain termination method using specific primers described in Barbas, C. F. et al., supra. Products of the sequencing reaction were analyzed on ABI prism 3100 genetic analyzer (Applied Biosystems, Foster, USA).

As a result, it was found that HSFN 68-13 Fab gene encodes $V_L$ and $V_H$ having the nucleotide sequences of SEQ ID NOs: 6 and 7, respectively; HSFN 68-16 Fab gene, $V_L$ and $V_H$ having the nucleotide sequences of SEQ ID NOs: 10 and 11, respectively; HSFN 68-27 Fab genes $V_L$ and $V_H$ having the nucleotide sequences of SEQ ID NOs: 14 and 15, respectively; and HSFN 68-41 Fab gene, $V_L$ and $V_H$ having the nucleotide sequences of SEQ ID NOs: 18 and 19, respectively.

The amino acid sequences of the Fab clones were deduced from the analyzed nucleotide sequences, respectively. It was found that $V_L$ and $V_H$ of HSFN 68-13 Fab had the amino acid sequences of SEQ ID NOs: 4 and 5, respectively; those of HSFN 68-16 Fab, the amino acid sequences of SEQ ID NOs: 8 and 9, respectively; those of HSFN 68-27 Fab, the amino acid sequences of SEQ ID NOs: 12 and 13, respectively; and those of HSFN 68-41 Fab, the amino acid sequences of SEQ ID NOs: 16 and 17, respectively.

As a result of analyzing FRs and CDRs in the amino acid sequences of the Fabs according to the method described in Harris et al., *Protein Science*, 4(2), p 306-310, 1995, the Fabs had the domain constitutions described in FIGS. 2 and 3.

Further, the light chain and heavy chain sequence homologies between HSFN 68 Fabs and SFN 68 Fab were 78 to 81% and 85 to 90%, respectively.

Example 4

Anti-HGF/SF Fab Expression and Purification for In Vitro Assay

Figure 4:
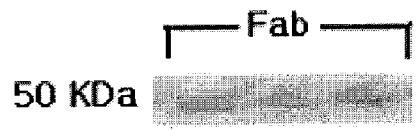
FIG. 4: the result of staining the purified Fab fragments of Example 4 with coomasie blue.

Non-suppressor *E. coli* strain HB2151 (Amersham Pharmacia Biotech) was transformed with Phagemid DNA of the clones selected in Example 2. The transformed bacteria were inoculated in 400 ml of LB medium containing 50 µg/ml of carbenicillin, and incubated at 30° C., 250 rpm until the OD at 600 nm reached 0.5 to 1.0, followed by induction with 1 mM IPTG at 30° C. overnight. Culture supernatants were concentrated by Labscale TFF system (Millipore, USA) purification, and subjected to the protein L column (Pierce Chemical Co, USA). The purified Fab fragments were confirmed by Coomassie staining, and the result is shown in FIG. 4.

Test Example 1

Analysis of the Binding Affinity Of Anti-HGF/SF Fab Humanized Antibody to HGF/SF The binding affinity of the anti-HGF/SF Fab humanized antibody to HGF/SF was determined by SPR (Surface plasmon Resonance) on a BIAcore device (BIAcore, Sweden).

Specifically, HGF/SF was immobilized on a carboxymethyldextran-modified (CM5) sensor chip (Biacore AB) using 10 mM sodium acetate buffer (pH 4.0) at a flow rate of 5 µl/min with an amine coupling kit (Biacore AB) in accordance with the instruction of the kit. Then 4 anti-HGF/SF Fabs and SFN 68 as a control dissolved in phosphate buffered saline (PBS, pH 7.4) containing 0.005% Tween 20 (Sigma) was injected on the chip at 25° C. for 2 min at a flow rate of 30 µl/min, respectively. The anti-HGF/SF Fab humanized antibody was diluted to a varying concentration in the range of 1.25 to 200 nM. The surface was regenerated with 1 M NaCl/50 mM NaOH. The kinetic rate constants ($k_{on}$ and $k_{off}$) as well as the equilibrium dissociation constant ($K_D$) were determined by using BIA evaluation software. The results are shown in Table 4.

TABLE 4

| clone | $k_{on}$ (M$^{-1}$s$^{-1}$) | $k_{off}$ (M$^{-1}$s$^{-1}$) | $K_D$ (M) |
|---|---|---|---|
| HSFN 68-13 | $6.47 \times 10^5$ | $1.35 \times 10^{-3}$ | $2.09 \times 10^{-9}$ |
| HSFN 68-16 | $3.24 \times 10^4$ | $1.39 \times 10^{-3}$ | $4.31 \times 10^{-8}$ |
| HSFN 68-27 | $3.92 \times 10^5$ | $2.07 \times 10^{-3}$ | $5.27 \times 10^{-9}$ |
| HSFN 68-41 | $1.06 \times 10^5$ | $1.12 \times 10^{-3}$ | $1.06 \times 10^{-8}$ |
| SFN 68 | $7.6 \times 10^3$ | $9.46 \times 10^{-5}$ | $1.24 \times 10^{-8}$ |

As can be seen in Table 4, HSFN68-13 Fab possessed the highest affinity to HGF/SF of the four variants tested, and this is about 6-fold tighter than for SFN68 control. HSFN68-16 showed the weakest affinity and the other clones HSFN68-27 and 41 exhibited equal affinity to HGF/SF.

Test Example 2

Competition Enzyme Immunoassay to Test the Neutralizing Effect of the Anti-HGF/SF Fab A 96-well microplate was coated with 1 μg/ml of HGF/SF and blocked by repeating the procedure of (2-2) of Example 2. Then 25 μl of 2 nM cMET/Fc chimera (R&D systems, USA) mixed with 25 μl of 0 to 200 nM HSFN 68-13 or SFN 68 dissolved in TBSB was added to the HGF/SF coated wells. The plate was incubated for at 37° C. 1 hour and washed with TBS-T. The amount of bound cMET/Fc chimera was assessed with HRP-conjugated rabbit anti-human Fc specific IgG (Pierce) using ultra-TMB substrate solution (Pierce) as a substrate. After 30 min incubation, optical density was measured at 450 nm. All experiments were performed in triplicates, and the average and standard deviation of the optical densities are listed in FIG. 5.

As can be seen in FIG. 5, HSFN 68-13 inhibited the binding HGF/SF to cMET/Fc chimera roughly in proportion to the clone concentration, and this neutralizing activity was equal to that of SFN 68.

Test Example 3

MDCK Scattering Assay

To test whether HSFN 68 Fab clones can neutralize the biological activity of HGF/SF, we employed MDCK scattering assay (see Thiery J. P. et al., *Nat. Rev. Cancer.*, 2, p 442-445, 2002) that has been most widely used to quantify the effect of inhibitors for HGF/SF and CMET signaling.

MDCK cells (Madine Darby canine kidney cells; ATCC CCL 34) were cultured in a DMEM medium supplemented with 10% FBS at 37° C. under 5% $CO_2$. Cells were distributed on each well of a 96-well plate at a concentration of $1.5 \times 10^3$ cells/well and incubated for 24 hours. Then, 18.75 μM of HGF/SF, preincubated with a mixture of 0 to 4.7 nM HSFN 68-13 and 0 to 700 ng/ml of polyclonal goat anti-human Fab specific IgG (Sigma) at 37° C. for 1 hour, was added to each well washed with PBS. The same procedure was repeated except for using SFN 68 as a control, and polyclonal goat anti-human Fab specific IgG or a mixture of non-specific Fab (Calbiochem Inc, USA) and goat anti-human Fab specific IgG as a negative control. After overnight treatment, the cells were fixed with a mixture of methanol and acetone (1:1 (v/v)), stained with 1% (w/v) aqueous crystal violet solution, and the scattering effect was monitored with a light microscope.

As can be seen in FIG. 6, MDCK cells treated with HGF/SF (B) were observed to scatter in contrast to the non-treated control MDCK cells (A). When HSFN 68-13 or SFN 68 is converted into a dimerized form by preincubation with the polyclonal goat anti-human Fab antibody, and added to the media (C and D), the scattering of MDCK was blocked and the result was equal to the control, while HSFN68-13 and SFN68 neutralized with 14.06 ng/ml of goat anti-human Fab polyclonal antibody at a minimal Fab concentration 187.5 μM. However, the polyclonal goat anti-human Fab specific IgG (E) and the mixture of non-specific Fab and goat anti-human Fab specific IgG (F) negative control did not show any inhibitory effect.

While the invention has been described with respect to the above specific embodiments, it should be recognized that various modifications and changes may be made and also fall within the scope of the invention as defined by the claims that follow.

What is claimed is:

1. An anti-HGF/SF (hepatocyte growth factor/scatter factor) humanized antibody which comprises:
   a) a heavy chain variable region ($V_H$); b) a light chain variable region ($V_L$);
   c) a heavy chain constant region identical to the human antibody heavy chain constant region; and
   d) a light chain constant region identical to the human antibody light chain constant region;
   wherein the $V_L$ and $V_H$ respectively have the amino acid sequences of:
   SEQ ID NOs: 4 and 5;
   SEQ ID NOs: 8 and 9;
   SEQ ID NOs: 12 and 13; or
   SEQ ID NOs: 16 and 17.

2. The humanized antibody of claim 1, which is a Fab.

3. A pharmaceutical composition comprising the humanized antibody of claim 1 as an active ingredient together with a pharmaceutically acceptable carrier.

* * * * *